United States Patent [19]

Dinius

[11] Patent Number: 4,519,798
[45] Date of Patent: May 28, 1985

[54] ABSORPTIVE STRUCTURE

[75] Inventor: Richard L. Dinius, Terre Haute, Ind.

[73] Assignee: Ethyl Corporation, Richmond, Va.

[21] Appl. No.: 411,555

[22] Filed: Aug. 25, 1982

[51] Int. Cl.³ ............................................ A41B 13/02
[52] U.S. Cl. .................................... 604/358; 604/366; 128/156
[58] Field of Search ................... 128/155, 156, 157; 604/358, 366, 370, 385

[56] References Cited

U.S. PATENT DOCUMENTS

| | | | |
|---|---|---|---|
| 3,446,208 | 5/1969 | Fukuda | 128/156 |
| 3,888,248 | 6/1975 | Moore et al. | 128/156 |
| 3,989,867 | 11/1976 | Sisson | 128/156 X |

*Primary Examiner*—John D. Yasko
*Attorney, Agent, or Firm*—Donald L. Johnson; John F. Sieberth; Paul H. Leonard

[57] ABSTRACT

An absorptive structure or device such as a disposable diaper or the like, for absorbing and containing fluid bodily discharges, comprising a liquid permeable top sheet, a liquid permeable carrier sheet adjacent thereto, an absorbent element adjacent the permeable carrier sheet and a liquid impermeable back sheet adjacent the absorbent element. The edges of the sheets are sealed together without glue or other adhesive composition so that the absorptive element is imprisoned between the sheets. Additional carrier sheets may be included in the structure as desired.

12 Claims, 3 Drawing Figures

ABSORPTIVE STRUCTURE

BACKGROUND OF THE INVENTION

The present invention relates to an absorptive structure or absorbent pad such as diapers, sanitary napkins, bed pads, incontinent pads, towels, bandages, and the like, and more particularly to absorptive structures or pads which freely allow fluids to pass into the interior of an absorptive device but which inhibit the reversal of the fluid. Such absorptive structures generally consist basically of a permeable top sheet, an absorptive element and a back sheet.

Presently, many absorbent pads such as baby diapers are made with a non-permeable sheet, i.e. non-permeable to the fluids being absorbed by the pad, an absorbent material and a permeable sheet. For ease in manufacture, the absorbent material has a carrier sheet on one or more sides thereof and the carrier material will not seal to either the permeable or impermeable sheet without some type of adhesive application during production.

Various types of fluid permeable top sheets have been constructed. For example, U.S. Pat. No. 3,814,107 issued to Kozak on June 4, 1974 illustrates a top sheet of a non-fibrous hydrophobic film which is provided with a plurality of valvular slits which restrict the reverse flow of liquid from the absorbent element of the device. U.S. Pat. No. 3,929,135 issued to Thompson on Dec. 30, 1975 describes a permeable top sheet which is provided with tapered capillaries of a particular pyramidal construction. Various degrees of success have been obtained with these prior art constructions.

It is therefore an important object of the present invention to provide an absorbent structure made of materials that will seal without the necessity of adding an adhesive during the production of the absorbent structure.

Other objects and advantages of the present invention will become readily apparent from a consideration of the following description and drawings wherein:

DESCRIPTION OF THE PREFERRED EMBODIMENTS

The discussion hereinafter is primarily directed to a disposable diaper. While this is contemplated as being a preferred absorptive structure or device, it should be understood that the product has substantial utility in a wide variety of absorptive devices, both disposable and reusable such as sanitary napkins, catamenial tampons, bed pads, incontinent pads, towels, bandages, and the like. A detailed description of the absorptive structure and its embodiment as a disposable diaper will allow one skilled in the art to readily adapt the invention to other devices.

Figure 1:
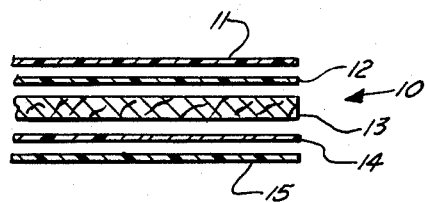
FIG. 1 is a cross-sectional view of a portion of a section of the absorbent structure of this invention illustrating the various layers of the structure.

In FIG. 1, the various layers or components of the absorptive structure of this invention are illustrated. For simplicity of illustration and understanding, the various layers are shown as being separated a greater distance than they normally would be. The structure or diaper 10 comprises a permeable top sheet 11, a permeable carrier sheet 12, a pad of absorbent material 13, a carrier sheet 14 and a non-permeable or back sheet 15. The carrier sheet 14 is optional and can be eliminated if desired. A plurality of carrier sheets 12 and/or 14 may be utilized in the structure 10, if desired. Such carrier sheets would be positioned approximately as sheets 12 and 14 are positioned in the absorptive structure 10.

Figure 2:
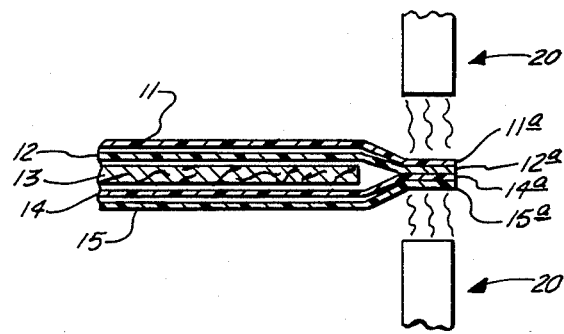
FIG. 2 is a view similar to FIG. 1 which illustrates the sealing of the edges of the various layers of the absorbent structure.
Figure 3:
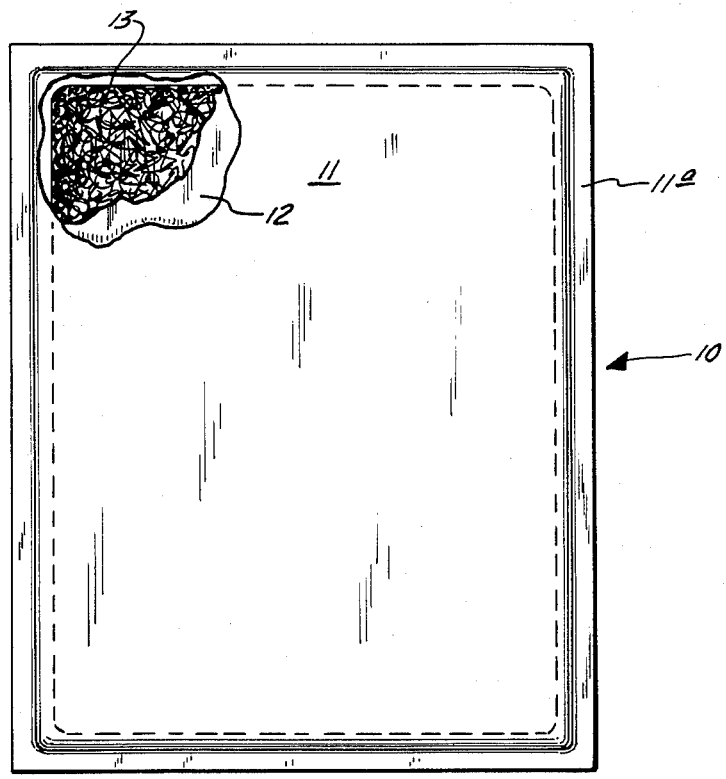
FIG. 3 is a plan view of the absorptive structure of this invention with a portion thereof removed and illustrating the area in which the various sheets are sealed together.

In FIG. 2, sheets 11, 12, 14, and 15 are each constructed of a material which will seal without the necessity of an adhesive. One manner of sealing is illustrated in FIG. 2, wherein a heat source 20 is provided for sealing the edges 11a, 12a, 14a and 15a of respective sheets 11, 12, 14, and 15. With all of the edges of the sheets sealed as illustrated in FIG. 2 and as seen in FIG. 3, the pad 13 is imprisoned or sealed within the various sheets or layers.

In a preferred absorptive structure, the top sheet, carrier sheets and back sheet are preferrably made from a polyolefin material. Polyethylene sheets are especially preferred. Polypropylene sheets are also suitable.

This invention provides a structure in which the diaper manufacturer or absorptive structure manufacturer can eliminate any glue or other adhesive compounds in the diaper or absorptive structure.

Practical absorptive devices such as disposable diapers must be constructed so that there is no reverse flow of fluid when the absorbent element is placed under pressure as by an infant or an adult sitting on or moving about in a wet disposable diaper. Protection from this pressure inducted reverse flow is obtained if the absorbent element is constructed so as to be less than totally saturated at its expected maximum fluid content. The absorbent element should be designed and constructed to contain a significantly larger quantity of fluid than it is anticipated that the absorptive device will be required to contain in any practical use situation. It is also important that the top sheet allow rapid transfer of liquids through it. The rate of transfer depends on a number of variables such as the rate of fluid discharges from the body, viscosity of the fluid, fraction of open area of the top sheet, diameter of the openings, etc. The proper combination of parameters for any given application can readily be determined by simple experimentation. The carrier sheet must also be constructed of a permeable material and may be of the same material as the top sheet or may be a different type of permeable material.

A permeable film having tapered capillaries having a base in the plane of the top sheet and an apex remote from the plane of the top sheet is especially sutitable. The top sheet, carrier sheets and back sheet are all constructed of materials in which the edges thereof may be sealed without the necessity of the addition of any glue or other adhesive composition, mixture or compound. Heat sealing materials are especially preferred.

A method and apparatus of making a permeable film is described in U.S. Pat. No. 4,272,473 issued to Riemersma, et al on June 9, 1981. The disclosure in this patent is hereby incorporated in this application.

The foregoing disclosure and description of the invention is illustrative and explanatory thereof and various changes in the illustrated process may be made within the scope of the appended claims without departing from the spirit of the invention.

What is claimed is:

1. An absorptive structure for absorbing and containing liquid bodily discharges comprising a liquid permeable topsheet of polyolefin film, a liquid permeable carrier sheet of polyolefin film, an absorbent element, and a liquid impermeable back sheet of polyolefin film, all of said sheets of polyolefin film having the edges thereof sealed to each other without the necessity of the addition of any glue or other adhesive composition, mixture or compound, and said absorbent element sealed within said sheets of polyolefin film.

2. The absorptive structure of claim 1, wherein said sheets of polyolefin film are polyethylene film.

3. The absorptive structure of claim 1, wherein a second liquid permeable carrier sheet of polyolefin film is added between said absorbent element and said impermeable back sheet.

4. The absorptive structure of claim 1 comprising a plurality of liquid permeable carrier sheets of polyolefin film positioned between the absorbent element and the liquid permeable top sheet of polyolefin film and/or positioned between said absorbent element and said impermeable back sheet.

5. The absorptive structure of claim 1, wherein said liquid permeable top sheet of polyolefin film and/or said liquid permeable carrier sheet are provided with tapered capillaries having a base in the plane of the sheet and an apex remote from the plane of the sheet.

6. The absorptive structure of claim 1, wherein the edges of said sheets of polyolefin film are heat sealed to each other.

7. A disposable diaper comprising a liquid permeable top sheet of polyolefin film, a liquid permeable carrier sheet of polyolefin film adjacent thereto, an absorbent element adjacent said liquid permeable carrier sheet, and a liquid impermeable back sheet of polyolefin film adjacent the absorbent element, all of said sheets of polyolefin film having the edges thereof sealed to each other without the necessity of the addition of any glue or other adhesive composition, mixture or compound, and said absorbent element sealed within said sheets of polyolefin film.

8. The disposable diaper of claim 7, wherein said sheets of polyolefin film are polyethylene film.

9. The disposable diaper of claim 7, wherein a second liquid permeable carrier sheet of polyolefin film is adjacent said liquid impermeable back sheet and said absorbent element.

10. The disposable diaper of claim 7, comprising a plurality of liquid permeable carrier sheets of polyolefin film positioned between said absorbent element and said liquid permeable top sheet of polyolefin film and/or positioned between said absorbent element and said impermeable back sheet.

11. The disposable diaper of claim 7, wherein said liquid permeable top sheet of polyolefin film and/or said liquid permeable carrier sheet are provided with tapered capillaries having a base in the plane of the sheet and an apex remote from the plane of the sheet.

12. The disposable diaper of claim 6, wherein the edges of said sheets of polyolefin film are heat sealed to each other.

* * * * *